US012751867B2

(12) United States Patent
Kreisel et al.

(10) Patent No.: US 12,751,867 B2
(45) Date of Patent: Oct. 6, 2026

(54) ABSORBENT ARTICLE COMPRISING A LOWER ACQUISITION AND DISTRIBUTION LAYER

(71) Applicant: The Procter & Gamble Company, Cincinnati, OH (US)

(72) Inventors: Sascha Kreisel, Frankfurt (DE); Gueltekin Erdem, Beijing (CN); Abhishek Prakash Surushe, Kelkheim (DE); Ernesto Gabriel Bianchi, Oberursel (DE); Yi Yuan, Beijing (CN); Adrien Grenier, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 563 days.

(21) Appl. No.: 17/826,202

(22) Filed: May 27, 2022

(65) Prior Publication Data

US 2022/0387227 A1 Dec. 8, 2022

(30) Foreign Application Priority Data

Jun. 1, 2021 (WO) ................ PCT/CN2021/097696

(51) Int. Cl.

*A61F 13/15* (2006.01)
*A61F 13/53* (2006.01)
*A61F 13/538* (2006.01)

(52) U.S. Cl.

CPC ...... *A61F 13/15203* (2013.01); *A61F 13/538* (2013.01); *A61F 2013/15406* (2013.01); (Continued)

(58) Field of Classification Search

CPC .............. A61F 13/15203; A61F 13/538; A61F 2013/15406; A61F 2013/15447; A61F 2013/530167; A61F 2013/530481
See application file for complete search history.

(56) References Cited

U.S. PATENT DOCUMENTS 5,989,688 A * 11/1999 Barge ........................ D04H 3/14 156/286
2002/0183704 A1* 12/2002 Fields ............... A61F 13/15203 604/374

(Continued)

FOREIGN PATENT DOCUMENTS

CN 1217644 A 5/1999
CN 103619291 A 3/2014

(Continued)

OTHER PUBLICATIONS

PCT Search Report and Written Opinion for PCT/CN2021/097696 dated Dec. 23, 2021,12 pages.

*Primary Examiner* — Philip R Wiest
*Assistant Examiner* — Seth Han
(74) *Attorney, Agent, or Firm* — Daniel S. Albrecht; Christian M. Best

(57) ABSTRACT

An absorbent article comprising a liquid-permeable topsheet, a liquid-impermeable backsheet, an absorbent material between the topsheet and the backsheet. The absorbent material comprising a superabsorbent polymer optionally mixed with cellulose fibers. The absorbent article comprises a lower acquisition and distribution layer disposed between the absorbent material and the backsheet, wherein the lower acquisition and distribution layer has a Strike-In below 10 seconds, as measured by the Strike-In test described herein, and a Median Desorption Pressure of less than 20 cmH2O, as measured by the Capillary Sorption Test Method.

16 Claims, 2 Drawing Sheets

(52) U.S. Cl.
CPC ............... *A61F 2013/15447* (2013.01); *A61F 2013/530167* (2013.01); *A61F 2013/530481* (2013.01)

(56) References Cited

U.S. PATENT DOCUMENTS

| | | | | |
|---|---|---|---|---|
| 2004/0127873 | A1* | 7/2004 | Varona | A61F 13/53756 604/385.01 |
| 2012/0323195 | A1* | 12/2012 | Ehrnsperger | A61F 13/15 604/366 |
| 2015/0094682 | A1* | 4/2015 | Fell | B32B 27/065 427/2.3 |
| 2016/0199527 | A1* | 7/2016 | Ota | A61L 15/26 502/402 |
| 2017/0258646 | A1* | 9/2017 | Grenier | A61F 13/51104 |
| 2019/0247238 | A1* | 8/2019 | Jackson | B32B 5/26 |
| 2019/0321243 | A1* | 10/2019 | Weber | B32B 37/22 |
| 2021/0030604 | A1* | 2/2021 | Van Malderen | A61F 13/513 |

FOREIGN PATENT DOCUMENTS

| | | | |
|---|---|---|---|
| EP | 2901993 | A1 | 8/2015 |
| EP | 3216434 | A1 | 9/2017 |
| JP | 2002506682 | A | 3/2002 |
| WO | 9955264 | A1 | 11/1999 |
| WO | 2018004564 | A1 | 1/2018 |

* cited by examiner

ABSORBENT ARTICLE COMPRISING A LOWER ACQUISITION AND DISTRIBUTION LAYER

FIELD

The present disclosure relates to absorbent articles for personal hygiene, such as baby diapers and adult incontinence products. The absorbent article comprises a lower acquisition and distribution layer disposed between the absorbent material and the backsheet.

BACKGROUND

Disposable absorbent articles for babies, toddlers and incontinent adults are widely used. These absorbent articles have a liquid permeable topsheet on the wearer-facing side, a liquid impermeable backsheet on the garment-facing side and an absorbent material. The absorbent material is disposed comprised in an absorbent core comprising an upper substrate layer and a lower substrate layer. Body fluid such as urine is acquired into the absorbent article through the topsheet and is ultimately absorbed and retained by the absorbent material. Superabsorbent polymer (SAP), especially in the form of particles, are the commonly used as absorbent material. The superabsorbent polymers may be mixed with cellulose fibers (in the context of absorbent articles also often referred to as “fluff pulp” or “airfelt”), but absorbent material free of cellulose fibers (“airfelt-free” cores) are also used.

Most personal absorbent hygiene articles have an acquisition layer directly under the topsheet. The acquisition layer provides fast acquisition of the fluid from the topsheet. In some absorbent articles, a distribution layer is further present between the acquisition layer and the absorbent core. The distribution layer distributes the fluid throughout the plane of the absorbent article to maximize the use of the absorbent material. The distribution layer may be in direct contact with the absorbent core.

Despite the existing acquisition and distribution layers, there remains a risk that a fluid cannot be absorbed into the absorbent core quickly enough, and thus flows through the absorbent core onto the backsheet. The acquisition layer or distribution layer may in some case not have sufficient void volume to temporarily hold the liquid before it can be absorbed into the absorbent material. Especially for absorbent cores with high percentage of superabsorbent polymer material, the void space provided by the super absorbent and absorption speed may not be fast enough to handle a larger amount of liquid in a sufficient manner (as superabsorbent polymer materials typically absorb liquid slower than cellulose fibers, especially when a first gush of liquid wet the article). A similar problem is encountered for absorbent core comprising channels, which are longitudinally elongated areas formed within the absorbent core that are substantially free of absorbent material. While the channels help distributing an insulting fluid along their length, the fluid can pass thought the channels and quickly get in direct contact with the backsheet.

While the backsheet is generally liquid impervious, moisture or vapor of liquid that pools between the absorbent core and the backsheet may nevertheless penetrate the backsheet, or cause a cold, damp and unpleasant feel when the backsheet is touched from the outside (e.g. by a caregiver). This effect is further increased when a breathable backsheet is used. Such damp feel may not only be unpleasant, but it may also lead to a premature diaper change long before the absorbent capacity of the absorbent article has been used up. Also, liquid, such as urine, that stays closer to the backsheet leads to increased visibility of stains from the outside through the backsheet.

There is thus a need for absorbent articles that address the above problems. Hence, it is an objective of the present disclosure to provide an absorbent article that has good fluid management properties and at the same time reduces or eliminates a cold and damp feel at the garment-facing surface of the backsheet.

It has been proposed to place an acquisition layer or a distribution layer between the absorbent core and the backsheet. Using a conventional upper acquisition and distribution layer however is not satisfactory to address the needs indicated above. The present disclosure addresses the problem of identifying tailored materials that can be used as lower acquisition and distribution layer to provide additional temporary storage while minimizing or preventing dampness perception from the outside surface of the absorbent article.

SUMMARY

In summary, the present disclosure is for an absorbent article comprising a liquid-permeable topsheet, a liquid-impermeable backsheet, and an absorbent material between the topsheet and the backsheet, the absorbent material comprising a superabsorbent polymer optionally mixed with cellulose fibers. The absorbent material is disposed between an upper substrate layer and a lower substrate layer. The lower acquisition and distribution layer is disposed between the absorbent material and the backsheet, wherein the lower acquisition and distribution layer has a Strike-In below 10 s, as measured by the Strike-In test described herein, and a Median Desorption Pressure (MDP) of less than 20 cmH2O, as measured by the MDP test described herein.

The inventors identified that standard measurements of fluid permeability in nonwoven materials, like strike-through and capillarity, are not sufficient to describe the behavior of a lower acquisition and distribution layer to enable an effective temporary storage of the body fluid exudates. The right void space to store fluid (porosity and caliper) is required to provide effective temporary storage. The inventors have found that the Strike-In value can reliably correlate to the combined effect of acquisition speed, mainly driven by porosity and nature or treatment of the fibers, and void volume for these temporary storage materials. The inventors have further found that the median desorption pressure (MDP) was an important parameter to mitigate negatives in wetness perception. Meeting the defined ranges of these two properties enable a lower acquisition and distribution layer having a combination of fibers, density and treatments that effectively provide the desired benefits of a temporary storage layers.

In a first aspect of the present disclosure, the lower acquisition and distribution layer is disposed between the lower substrate layer and the backsheet.

In a second aspect of the present disclosure, the lower acquisition and distribution layer and the lower substrate layer are the same layer.

In a third aspect of the present disclosure, the lower acquisition and distribution layer is disposed between the absorbent material and the lower substrate layer.

The lower acquisition and distribution layer may be comprised of a single layer. Alternatively, the lower acquisition and distribution layer may be a multi-layer construction. The lower acquisition and distribution layer may in particular comprise or consists of a nonwoven layer having the Strike-In and MDP properties indicated above.

BRIEF DESCRIPTION OF THE DRAWINGS

While the specification concludes with claims particularly pointing out and distinctly claiming the present disclosure, it is believed that the same will be better understood from the following description read in conjunction with the accompanying drawings in which:

DETAILED DESCRIPTION

Definitions

Figure 1:
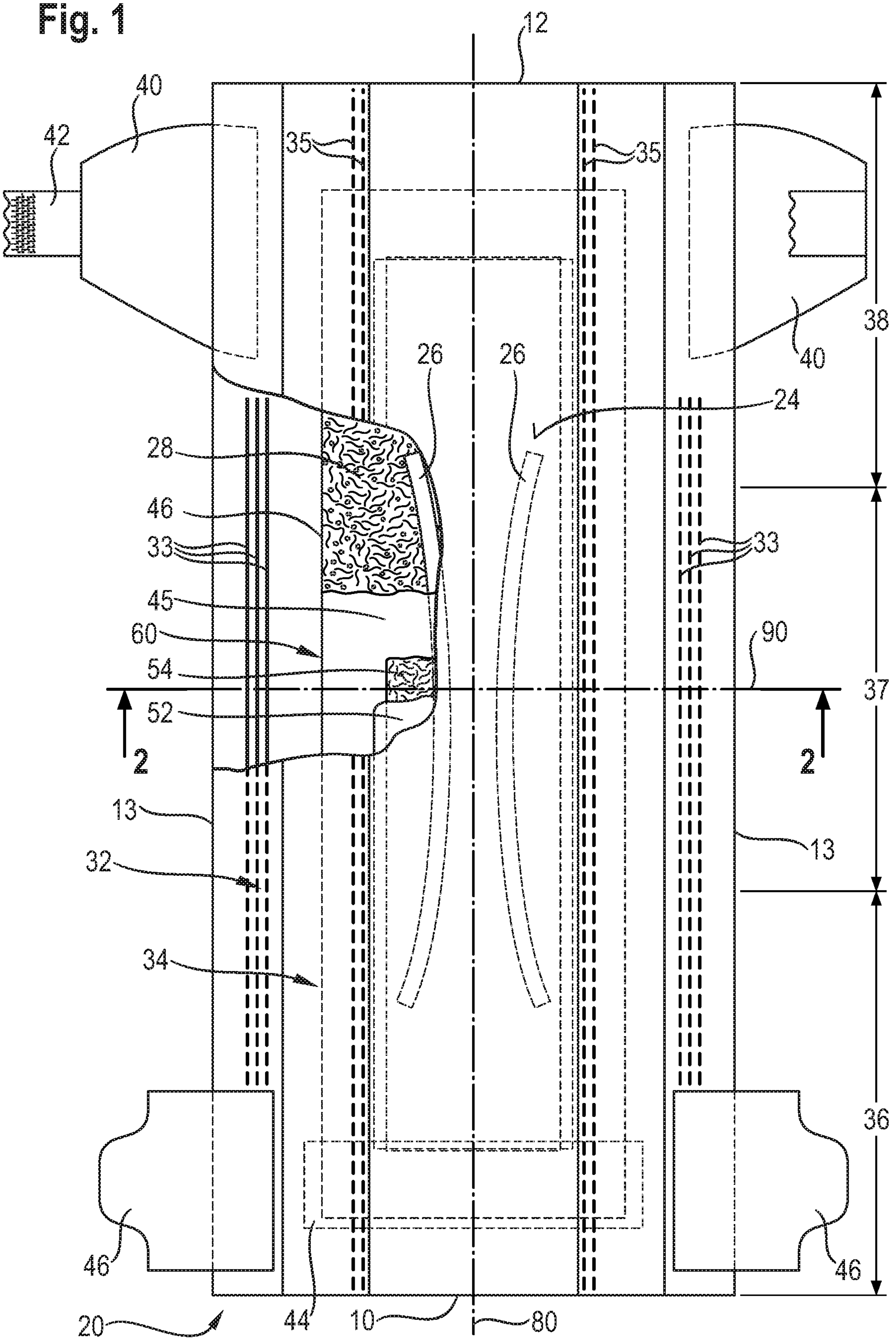
FIG. 1 is an exemplary absorbent article in the form of a diaper.

As used herein, "absorbent article" refers to devices that absorb and contain body exudates, and, more specifically, refers to devices that are placed against or in proximity to the body of the wearer to absorb and contain the various exudates discharged from the body. Absorbent articles include diapers (baby and infant diapers as well as diapers for adult incontinence), pants (for babies, infants and for adults), absorbent inserts (which are intended to be inserted into an outer cover to form a diaper or pant), feminine care absorbent articles such as sanitary napkins and pantiliners, and the like. As used herein, the term "exudates" includes, but is not limited to, urine, blood, vaginal discharges, sweat and fecal matter. Preferred absorbent articles of the present disclosure are disposable absorbent articles, more preferably disposable diapers and disposable pants.

As used herein, "diaper" and "pant" refers to an absorbent article generally worn by babies, infants and incontinent adults about the lower torso so as to encircle the waist and legs of the wearer and that is specifically adapted to receive and contain urinary and fecal waste. In a pant, as used herein, the longitudinal edges of the first and second waist region are attached to each other to a pre-formed waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using re-fastenable and/or non-refastenable bonds (e.g., seam, weld, adhesive, cohesive bond, fastener, etc.). A pant may be pre-formed anywhere along the circumference of the article (e.g., side fastened, front waist fastened). In a diaper, the waist opening, and leg openings are only formed when the diaper is applied onto a wearer by (releasable) attaching the longitudinal edges of the first and second waist region to each other on both sides by a suitable fastening system.

As used herein, the terms "nonwoven", "nonwoven web" and "nonwoven layer" are used interchangeably. Nonwovens are broadly defined as engineered fibrous assemblies, primarily planar, which have been given a designed level of structural integrity by physical and/or chemical means, excluding weaving, knitting or paper making. The fibers may be of natural origin, such as cotton or bamboo fibers, or man-made origin. Synthetic fibers may be selected from the group consisting of polyolefins (such as polyethylene, polypropylene or combinations and mixtures thereof), polyethylene terephthalate (PET), co PET, polylactic acid (PLA), polyhydroxy alkanoid (PHA), or mixtures or combinations thereof. The fibers may be staple fibers (e.g. in carded nonwoven webs/layers) or continuous fibers (e.g. in spunbonded or meltblown nonwoven webs/layers).

Nonwoven webs/layers can be formed by many processes such as meltblowing, spunlaying, solvent spinning, electrospinning, and carding, and the fibers can be consolidated, e.g. by hydroentanglement (in spunlaced nonwoven webs/layers), air-through bonding (using hot air that is blown through the fiber layer in the thickness direction), needle-punching, one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g. by spraying, printing or foam application) and is subsequently cured to solidify. The basis weight of nonwoven fabrics is usually expressed in grams per square meter ($g/m^2$).

"Monocomponent" refers to fibers formed of a single polymer component or single blend of polymer components, as distinguished from bicomponent or multicomponent fiber.

"Bicomponent" refers to fibers having a cross-section comprising two discrete polymer components, two discrete blends of polymer components, or one discrete polymer component and one discrete blend of polymer components. "Bicomponent fiber" is encompassed within the term "multicomponent fiber." A bicomponent fiber may have an overall cross section divided into two subsections of the differing components of any shape or arrangement, including, for example, concentric core-and-sheath subsections, eccentric core-and-sheath subsections, side-by-side subsections, radial subsections, etc.

"Multicomponent fiber" includes, but is not limited to, "bicomponent fiber." A multicomponent fiber may have an overall cross section divided into subsections of the differing components of any shape or arrangement, including, for example, coaxial subsections, concentric core-and-sheath subsections, eccentric core-and-sheath subsections, side-by-side subsections, islands-in the sea subsection, segmented pie subsections, etc.

Nonwoven materials can be formed by a variety of fiber materials (PP, PE, PET, coPET, bicomponent, and mixture thereof) and, in some cases, the fibers or the nonwovens can be treated to enhance specific fluid handling characteristics, such as fluid permeability or fluid barrier properties.

The term "dtex" as used herein refers to a unit used to indicate the fineness of a filament/fiber. The unit expresses the mass of a filament/fiber in grams per 10,000 meters of length.

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is greater than 90° and the fluid does not spread spontaneously across the surface of the fiber.

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Inner" and "outer" refer respectively to the relative location of an element or a surface of an element or group of elements. "Inner" implies the element or surface is oriented towards the inside of the article while "Outer" implies the element or surface is oriented towards the outside of the article.

"Body-facing" and "garment-facing" refer respectively to the relative location of an element or a surface of an element or group of elements. "Body-facing" implies the element or surface is nearer to the wearer during wear than another element of the same component. "Garment-facing" implies the element or surface is more remote from the wearer during wear than another element of the same component. The garment-facing surface may face another (i.e. other than the wearable article) garment of the wearer, other items, such as the bedding, or the atmosphere.

General Description of an Exemplary Diaper

FIG. 1 is a plan view of an exemplary diaper 20, in a flat-out state, with portions of the diaper being cut-away to more clearly show the construction of the diaper. This diaper 20 is shown for illustration purpose only as the structure of the present disclosure may be comprised in a wide variety of diapers or other absorbent articles, such as pants having pre-formed side seams. The side seams of pant articles can be opened by cutting or otherwise, if it is desired to place the pant in a flattened out configuration.

As illustrated in FIG. 1-2, the absorbent article comprises a topsheet 24, backsheet 25, and an absorbent material 28 which is positioned between the topsheet 24 and the backsheet 25. The absorbent material 28 typically forms a layer having a pre-determined shape in the plane formed by the article when flattened-out. The layer of absorbent material may be substantially rectangular as illustrated in FIG. 1, or have another shape such as a tapered outline as in a sand-hour shape. The layer of absorbent material 28 may further comprise longitudinally-oriented channels 26, which are areas substantially free of absorbent material, that facilitate the distribution of a fluid along the length of the absorbent article.

Absorbent articles, such as the diaper 20 illustrated in FIGS. 1-2, typically comprise an (upper) acquisition layer 52 directly bonded underneath the topsheet, and optionally a distribution layer 54. Typical acquisition layers 52 are surfactant treated, latex bonded nonwoven acquisition layer. The distribution layer 54 may consist of cross-linked cellulose fibers, as is known in the art. The prior art discloses many types of acquisition-distribution layers, see for example WO2000/59430, WO95/10996, U.S. Pat. No. 5,700,254, WO02/067809.

The absorbent article 20 may also comprise inner barrier leg cuffs 32 and outer leg cuffs 34, as is known in the art. The inner barrier cuffs 34 can extend upwards from the surface of the article to provide retention of the waste, while the outer cuffs are typically formed in the plane of the chassis of the article as defined by topsheet and backsheet. These cuffs are preferably elasticized, as is known in the art, for example using elastic threads 33, 35 as represented in the Figures. Moreover, the absorbent article may comprise a fastening system, such as an adhesive fastening system or a hook and loop fastening member, which can comprise tape tabs 42 disposed on back ears 40, such as adhesive tape tabs or tape tabs comprising hook elements, cooperating with a landing zone 44 (e.g. a nonwoven web providing loops in a hook and loop fastening system). While taped diapers typically comprise back ears 40, and front ears 46, these are typically not present in pant-type absorbent articles having pre-formed side seams.

The front and/or back ears 40, 46 may be separate components attached to the absorbent article or may instead be continuous with portions of the topsheet and/or backsheet such that these portions form all or a part of the front and/or back ears 40, 46. Also combinations of the aforementioned are possible, such that the front and/or back ears 40, 46 are formed by portions of the topsheet and/or backsheet while additional materials are attached to form the overall front and/or back ears 40, 46. The front and/or back ears may be elastic or non-elastic. Also, the front ears 40 may be applied as separate components attached to the absorbent article while the back ears (or parts thereof) 46 may be continuous with portions of the backsheet and/or topsheet—or vice versa.

The absorbent article, whether diaper or pant, can be notionally divided in a first waist region 36 (which may be the front waist region), a second waist region 38 (which may be the back waist region) opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened-out diaper and going through the middle of the length of the diaper (the same applies to for the transversal centerline and longitudinal line of other absorbent articles of the present disclosure). The periphery of the diaper 20 is defined by the outer edges of the diaper. The longitudinal edges 13 of the diaper may run generally parallel to the longitudinal centerline 80 of the diaper 20 and the end edges (the front waist edge 10 and the back waist edge 12) run between the longitudinal edges generally parallel to the transversal centerline 90 of the diaper 20. The crotch region, the first and the second waist region each constitute ⅓ of the absorbent article along the longitudinal centerline.

Further, the absorbent article may comprise other optional but conventional elements, which are not represented for simplicity, such as an elastic back waist feature, a front waist elastic feature, a lotion applied onto the body-facing surface of the topsheet, or a urine indicator disposed on the inner side of the backsheet that changes color when contacted with urine.

The topsheet 24, the backsheet 25, and the layer of absorbent material 28 may be assembled in a variety of well-known configurations, in particular by gluing, heat embossing, ultrasonic bonding or combinations thereof. Exemplary diaper configurations are described generally in U.S. Pat. Nos. 3,860,003; 5,221,274; 5,554,145; 5,569,234; 5,580,411; and 6,004,306.

The topsheet 24 is the part of the absorbent article 20 that is in contact with the wearer's skin. At least a portion of, or all of, the topsheet is liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polypropylene or bicomponent PE/PP fibers or mixtures thereof), or a combination of natural and synthetic fibers. The topsheet may have one or more layers. The topsheet may be apertured or non-apertured, and may have any suitable three-dimensional features, and/or may have a plurality of embossments (e.g., a bond pattern). Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet 25 is generally that portion of the absorbent article 20 that constitutes all or a part of the garment-facing surface of the absorbent article. The backsheet 25 may be joined at least partially to the topsheet 24, the absorbent material 28, the substrate layer 46, or the lower acquisition and distribution layer 60, by any attachment methods known to those of skill in the art. The backsheet 25 prevents, or at least inhibits, the bodily exudates absorbed and contained in the absorbent material 28 from soiling articles such as bedsheets, undergarments, and/or clothing. The backsheet is typically liquid impermeable, or at least substantially liquid impermeable.

The backsheet 25 is typically comprised of a thin impermeable plastic film, usually a thermoplastic film having a thickness of about 0.01 mm to about 0.05 mm. The backsheet material may be breathable, which permit vapors to escape from the absorbent article, while still preventing, or at least inhibiting, bodily exudates from passing through the backsheet. A breathable backsheet may have a Water Vapor Transmission Rate (WVTR) of from 1,000 to 15,000 $g/m^2/24$ h, or from 1,000 to 10,000 $g/m^2/24$ h, or from 1,500 to 10,000 $g/m^2/24$ h as measured using a PERMATRAN-W Model 101K (available from Mocon, Inc., Minneapolis, MN) or equivalent, according to Nonwovens Standard Procedure NWSP 70.4.R0(15) with the following specifications: experiments were carried out in a lab controlled at 23° C.±2° C. and 50% RH±2% RH and the instrument cells heated to 37.8° C. (100° F.).

The backsheet 25 may also comprise a backsheet outer cover nonwoven (not represented). The backsheet outer cover nonwoven is typically a thin nonwoven material that is joined to the outer surface of the backsheet film. The outer cover nonwoven may thus form the garment-facing surface of the backsheet. The backsheet outer cover nonwoven may comprise a bond pattern, apertures, and/or three-dimensional features, and may improve the feel of the backsheet.

The absorbent material 28 typically comprise superabsorbent polymer particles, which may be optionally mixed with cellulose fibers. The absorbent material may also be free of cellulose fibers mixed with the superabsorbent polymer particles, with the superabsorbent particles being immobilized by a microfibrous net of adhesives, or alternatively supported within a high loft, porous nonwoven, as is known in the art.

The absorbent material 28 is typically disposed between an upper substrate layer 45 oriented towards the topsheet and a lower substrate layer 46 oriented towards the backsheet, forming an absorbent core. The upper substrate and lower substrate layer are commonly referred to respectively as core cover and dusting layer, and together as core wrap. These substrate layers are typically low basis weight nonwoven, (typically less than 20 gsm, in particular less than 14 gsm), and may be in particular SMS nonwoven (Spunbond-Meltblown-Spunbond laminate), as is known in the art. The absorbent material and the substrate layers are commonly referred to as the absorbent core in the art.

The upper and the lower substrate layers 45, 46 may be made of the same material, i.e. of the same nonwoven web, such as a single, continuous nonwoven web, which is wrapped around the layer of absorbent material, e.g. in a c-wrap configuration. The substrate layers may be made of the same or different materials, i.e. two nonwoven webs which have the same of different properties.

Figure 2A:
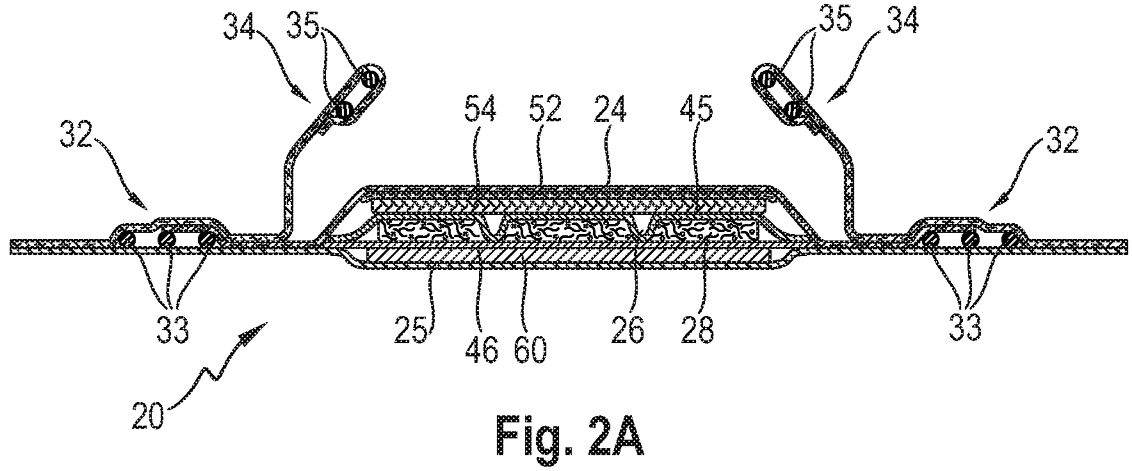
FIG. 2A is a transversal cross-section of the diaper of FIG. 1 showing a lower acquisition and distribution layer between the lower substrate layer and the backsheet.
Figure 2B:
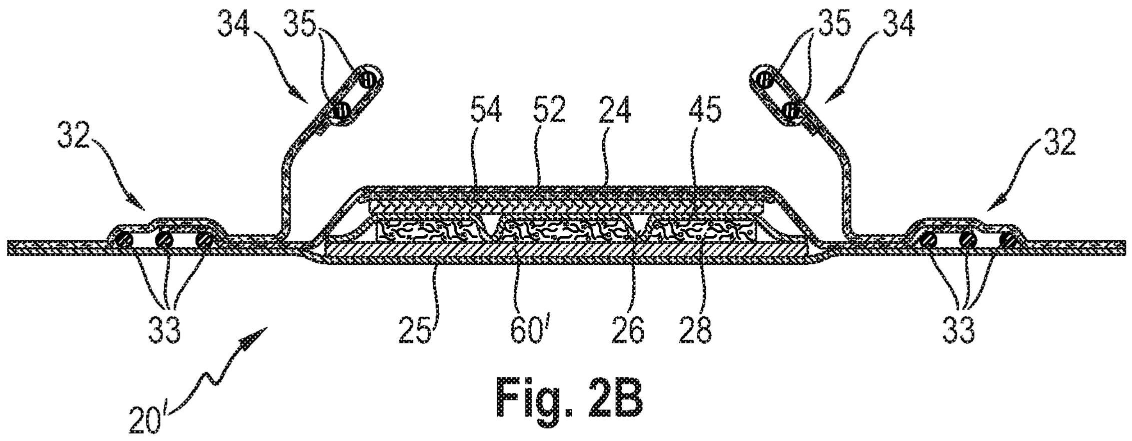
FIG. 2B is an alternative transversal cross-section of the diaper of FIG. 1, wherein the lower acquisition and distribution layer and the lower substrate layer are the same layer.
Figure 2C:
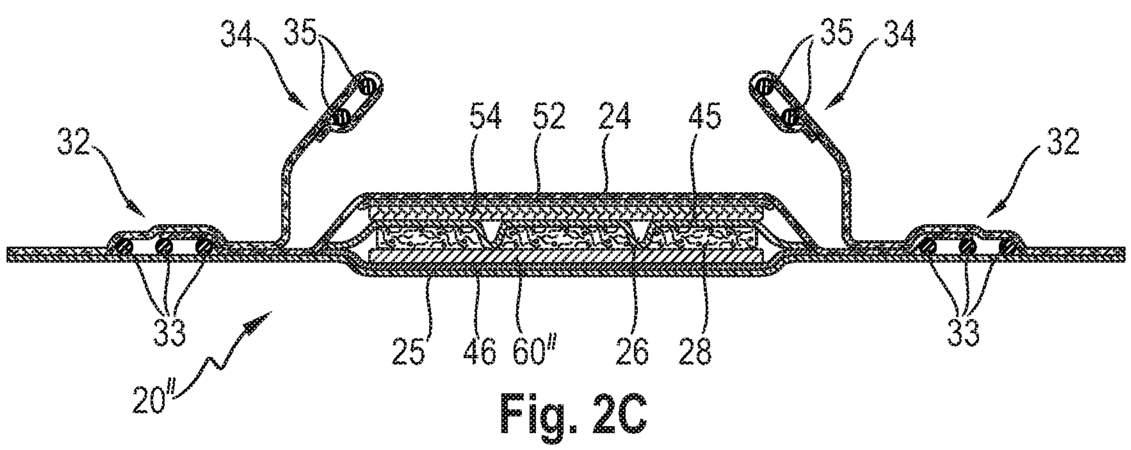
FIG. 2C is an alternative transversal cross-section of the diaper of FIG. 1, wherein the lower acquisition and distribution layer is disposed between the absorbent material and the lower substrate layer.

The substrate layers are preferably bonded longitudinally to prevent the absorbent material from being released sideways. The substrate layers may also be optionally bonded transversally at the front and the back of the absorbent core. The substrate layers may be bonded face to face, at least longitudinally as represented in FIGS. 2a-2c, but other bonding configurations are possible, in particular a C-wrap configuration where one of the top or bottom substrate layer is larger than the other, so that flaps can be folded around the absorbent material and attached to the other substrate. Portions at and adjacent to the longitudinal edges of the upper substrate layer 45 may be folded over the longitudinal edges of the layer of absorbent material, such that these portions are positioned on the garment-facing surface of the layer of absorbent material. Alternatively, or in addition, portions at and adjacent to the longitudinal edges of the lower substrate layer 46 may be folded over the longitudinal edges of the layer of absorbent material, such that these portions are positioned on the body-facing surface of the layer of absorbent material.

The upper substrate layer 45 and the lower substrate layer 46 typically least partially or fully enclose the absorbent material 28, providing for dry and wet immobilization of the absorbent material. Additionally, the absorbent material may be immobilized on the upper substrate layer 45 and/or on the lower substrate layer 46, and/or on the lower ADL 60, for example by use of hot melt adhesive.

The upper and lower substrate layer 45, 46 may be any material capable of providing a support for the absorbent material. It may be a web or sheet material, such as foam, film, woven or, preferably, a nonwoven web. For those absorbent articles that do not require an upper acquisition-distribution layer or system 52, 54, then the upper substrate layer 45 is provided directly between the topsheet 24 and the absorbent material 28.

The lower substrate layer 46 is typically provided between the absorbent material 28 and the lower ADL 60 as represented in FIG. 2A. In other words, the lower ADL 60 is typically disposed between the lower substrate layer 46 and the liquid-impermeable backsheet 25. This construction is also the simplest to make, as it does not require making changes to existing absorbent core making process, the lower ADL being additionally interposed between the absorbent core and the backsheet.

Alternatively, it is also considered that the lower ADL 60' may in some cases replace the lower substrate layer 46 and be in direct contact with the absorbent material 28 (so that there is no separate lower substrate layer 46). In this case, the upper substrate layer 45 and the lower ADL 60' may partly or fully enclose the layer of absorbent material 28. This embodiment is represented in FIG. 2B for alternative absorbent article 20'. However, such construction has drawbacks, as it require the lower ADL 60' to be larger and longer than necessary to cover the entire layer of absorbent material 28, which has additional material costs. The material cost of the lower ADL is typically a multiple of the costs of a low basis weight nonwoven than ca be used lower substrate layer 46. Thus, it may be preferred that the absorbent article comprises a lower substrate layer 46 and a separate lower ADL 60, as illustrated in FIG. 2A and FIG. 2C.

In another alternative, as illustrated in FIG. 2C, the absorbent material 28 and the lower ADL 60" may be partially or fully enclosed between the upper substrate layer 45 and lower substrate layer 46. The lower acquisition and distribution layer 60" is disposed in this alternative between the absorbent material 28 and the lower acquisition substrate layer 46. This embodiment however adds complexity to the forming process, and superabsorbent particles may penetrate the pores of the ADL impacting its fluid handling properties.

The absorbent material 28 comprises a superabsorbent polymer, such as in the form of superabsorbent polymer particles, and may optionally comprise cellulose fibers. The absorbent material may comprise at least 30 weight-%, or at least 40 weight-%, or at least 50 weight-%, or at least 60 weight-%, or at least 70 weight-%, or at least 80 weight-% or at least 90 weight-% of superabsorbent polymer, such as superabsorbent polymer particles, by total weight of the absorbent material. The absorbent material may comprise up to 70 weight-% of cellulose, or up to 50 weight-% of cellulose, in particular less than 25 weight-%, or less than 20 weight-%, or less than 15 weight-%, or less than 10 weight-% of cellulose, or less than 5% by weight of cellulose, or even no cellulose based on the total weight of the layer of absorbent material.

The superabsorbent polymer particles and the cellulose fibers may be homogeneously mixed with each other such that the ratio of cellulose fibers to superabsorbent polymer particles is substantially the same throughout the layer of absorbent material. Alternatively, the superabsorbent polymer particles and the cellulose fibers may be non-homogeneously mixed such that the ratio of cellulose fibers to superabsorbent polymer particles is higher towards the front and rear edges of the layer of absorbent material compared to a central area of the layer of absorbent material. The area towards the front edge of the layer of absorbent material, the area towards the rear edge of the layer of absorbent material, and the central area may each extend along ⅓ of longitudinal dimension of the layer of absorbent material along the longitudinal centerline.

When the layer of absorbent material is cellulose free, the only absorbent material in the absorbent layer may be superabsorbent polymer (particles, fibers or foam). The resulting layer of absorbent material has a reduced thickness in the dry state compared to conventional absorbent cores including cellulosic fibers. The reduced thickness helps to improve the fit and comfort of the absorbent article for the wearer.

The layer of absorbent material 28 defines a deposition area, when considered in the plane of the absorbent article as shown in FIG. 1, having a pre-determined shape. The absorbent layer 28 may have any shape, in particular a rectangular shape as illustrated in FIG. 1, but other shapes are common such as dog-bone or sand-hour shaped having a tapering in the crotch region of the article.

The absorbent material 28 may define one or more channel(s) 26, where substantially no absorbent material is present, apart possibly from accidental discrete contamination. These channels preferably do not extend to any of the side of the absorbent layer, and thus the channels are completely surrounded by the absorbent material. The channels are typically elongated in the longitudinal direction, having a length of from 20% and 80%, or from 20% to 70%, or from 30% to 60%, by total longitudinal dimension of the layer of absorbent material 28. The channel may be straight, curved, or combinations thereof. The channels are typically symmetrically disposed relative to the longitudinal axis, and may be disconnected from another, as illustrated in FIG. 1, alternatively the channels 26 may be connected at one or both their extremities to form a U or O shape. Such channels are disclosed in further details e.g. in WO2012170778A1, WO2012170781 (Kreuzer et al.).

The upper substrate layer 45 and lower substrate layer 46 may be bonded to each other through at least a portion of the length of the channel. This bond provides for structural integrity of the channels in dry and wet state. Any known bonding techniques known in the art may be used to provide for this bond, in particular one selected from adhesive bonding, thermo bonding, mechanical bonding, ultrasonic bonding, or any combinations thereof. An adhesive may be for example applied in the areas of the channels on the inner side of the top side and/or the inner side of the bottom side of the core wrap, typically by slot glue application or any other means, followed by the application of pressure in the areas of the channels to provide a good adhesive bonding in these areas. Exemplary patent disclosures of such adhesive bonding processes can be found for an airfelt or airfelt-free absorbent cores in WO2012/170798A1 (Jackels et al.), EP2,905,000 (Jackels et al.) and EP2,905,001 (Armstrong-Ostle et al.).

Other bonding such as thermo bonding, mechanical bonding, ultrasonic bonding can also be used as additional bonding or as an alternative bonding. For example, an adhesive bonding may be reinforced by a thermo bonding, mechanical bonding or ultra-sonic bonding. Such thermo, mechanical or ultrasonic bonding can be applied on the channels through the external sides of the core wrap substrates.

Typically, the bonds may generally have the same outline and shape as the channels 26 in which they are contained, but may be slightly smaller to allow for a safety margin (e.g. by a few mm) as some deviations from the optimal registration may happen during high speed process. The channels may also be not bonded, or have one or more section which is bonded and one or more section that is not bonded.

The absorbent article may comprise at least one channel which is at least partially vertically superposed with the lower acquisition and distribution layer, preferably wherein at least 50% of the channel area is vertically superposed with the lower acquisition and distribution layer. By "vertically it is meant in the direction perpendicular to the plane formed by the transverse and longitudinal centerlines.

Suitable SAP may be any water-insoluble, water-swellable polymers capable of absorbing large quantities of fluids, as is known in the art. The term "superabsorbent polymer" refers herein to absorbent materials, typically cross-linked polymeric materials, that can absorb at least 10 times their weight of an aqueous 0.9% saline solution as measured using the Centrifuge Retention Capacity (CRC) test (EDANA method WSP 241.2.R3 (12)). The SAP may in particular have a CRC value of more than 20 g/g, or more than 24 g/g, or of from 20 to 50 g/g, or from 20 to 40 g/g, or 24 to 35 g/g.

Lower Acquisition and Distribution Layer (Lower "ADL") 60

The lower ADL 60 is disposed between the absorbent material 28 and the backsheet 25. If the absorbent article comprises a lower substrate layer 46 that, in conjunction with an upper substrate layer 45 at least partially encloses the layer of absorbent material 28, the lower ADL may be typically disposed in direct contact between the backsheet 24 and the lower substrate layer 45 as illustrated in FIG. 2A. However other configurations are possible, as illustrated in FIGS. 2B and 2C discussed above for example.

As indicated in the summary, the inventors have identified that standard measurements of fluid permeability in nonwoven materials, like strike-through and capillarity, are not sufficient to describe the behavior of a lower acquisition and distribution layer to enable an effective temporary storage of the body fluid exudates. The right void space to store fluid (porosity and caliper) is required to provide effective temporary storage. The inventors have found that the Strike-In value measures the combined effect of acquisition speed and void volume on these temporary storage materials. The inventors have further found that the median desorption pressure (MDP) was an important parameter to mitigate negatives in wetness perception. Meeting the defined ranges of these two properties enable a lower acquisition and distribution layer having a combination of fibers, density and treatments that effectively provide the desired benefits of a temporary storage layers.

According to the present disclosure, it was found that when the lower acquisition and distribution layer has a Strike-In below 10 s, preferably below 8 as measured by the Strike-In test described herein, and a Median Desorption Pressure (MDP) of less than 20 cmH2O, preferably less than 15 cmH2O as measured by the MDP test described herein, the absorbent article retains good acquisition properties, while at the same time avoiding that the liquid pools in the vicinity from the backsheet (see data in the example section below).

While not wishing to be bound by theory, it is believed that lower values of the Strike-In time indicates the material allows faster speed of acquisition in the lower ADL, improving overall absorbency of the absorbent article as it provided a functionality of a temporary storage for the fluid exude. The Strike-In time diminishes with increased permeability of the layer and increased void space in the substrate. Values below 10 seconds shows benefits on improving the overall acquisition speed of the absorbent article. Median Desorption Pressure or MDP (measured in centimeter H2O) measures the drainage properties of the material, or how easy the material can be dewatered by the absorbent material. The lower the MDP the easier to dewater the lower ADL layer.

The lower ADL may be comprised of a single layer, in particular a single nonwoven layer having the required properties. Alternatively, it is not excluded that the lower ADL may be a multi-layer construction such as a laminate or an integrated layer comprising integrated sub-layers, as long as the multi-layer construction having the required properties. If the absorbent article comprises a separate lower substrate layer forming the bottom layer of the core wrap, this separate lower substrate layer having a basis weight below 20 g/m$^2$, is not considered as part of the lower ADL.

The lower ADL 60 may be comprised or consists of a nonwoven layer having the required properties. Nonwoven layers are commonly used in absorbent articles and can be cut, disposed and attached in the absorbent article using conventional techniques known in the art. The lower ADL may in particular comprises or consists of a single nonwoven layer having the Strike-In and MDP properties indicated above.

Commonly used nonwoven materials in the absorbent articles industry can be formed by a variety of fiber materials (PE, PP, PET, coPET, Bico, or mixes of those fibers within others) and, in some cases, the fibers or the nonwovens can be treated to enhance specific fluid handling characteristics such as fluid permeable layers or fluid impermeable barriers.

The lower ADL may serve as a temporary reservoir for liquid that has flown through the layer of absorbent material because it was not absorbed fast enough by the absorbent material of the layer of absorbent material.

Additional layers provided to an absorbent article generally increase the thickness and bulk of the article, thereby reducing wearer comfort. Also, increased bulk is generally not desirable, especially between the wearer's legs. Therefore, it may be desirable to limit the caliper of the lower ADL to be in the range of from 0.3 mm optionally up to e.g. 4 mm, measured at 0.85 kPa pressure according to the Caliper Measurement Method described herein.

The basis weight of the lower ADL may typically (but not necessarily) be in the range of from 20 g/m$^2$ to 100 g/m$^2$, or from 25 g/m$^2$ to 80 g/m$^2$, or from 30 g/m$^2$ to 50 g/m$^2$. The basis weight of the lower ADL, at least when comprised of a single layer, is typically homogeneous throughout the length and width of the lower ADL (i.e. in the longitudinal and transverse direction). The basis weight of a material is typically provided by the supplier, and if not can be calculated by dividing the weight of the lower ADL by its surface.

The lower ADL may have a smaller extension in the longitudinal and/or transverse direction than the layer of absorbent material 28, such that the layer of absorbent material extends beyond the lower ADL in longitudinal and/or transverse direction. The layer of absorbent material may also extend beyond the upper ADS in the longitudinal and/or transverse direction.

Alternatively, the lower ADL may have a larger extension in the longitudinal and/or transverse direction than the layer of absorbent material, such that the lower ADL extends beyond the layer of absorbent material in the longitudinal and/or transverse direction. This may be desirable when the layer of absorbent material is in direct contact with the lower ADL (i.e. when there is no lower substrate layer between the layer of absorbent material and the lower ADL). In such configurations, the layer of absorbent material may be partly or fully deposited and formed on the lower ADL. The layer of absorbent material may be partly formed on the lower ADL and partly on an upper substrate layer, and subsequently, both sub-components of the layer of absorbent material are combined to form the layer of absorbent material by putting the two sub-components in a face to face relationship.

The lower ADL may be typically free of superabsorbent polymer. The lower ADL may comprise or consist of a nonwoven layer. The nonwoven layer may be any type of conventional nonwovens and fibers, as long as the properties required are met. Carded nonwovens (made of staple fibers) were found particularly suitable. Carded nonwovens may be calendar bonded or air-through bonded, as is known in the art. The nonwoven layer may also be a spunbond or meltblown nonwoven web (made of continuous fibers) or a nonwoven with spunbond and meltblown layers (e.g. an SMS, SMMS, SMSS or the like).

Air-through bonded nonwoven generally have high loft. Hence, they have a porous structure to provide void volume for absorbing and temporarily holding liquid. At the same time, they provide softness and do not have an excessively high bending stiffness.

The lower ADL may comprise at least 30 weight %, optionally at last 50% and up to 100 weight % of crimped fibers based on the total weight of the lower acquisition and distribution layer. The crimped fibers may have two-dimensional crimp, three dimensional crimp or a combination of two- and three-dimensional crimp. Typically, in the carded process, all or most fibers are two-dimensionally crimped (zigzag), whereas eccentric bicomponent fibers may be typically three-dimensional crimped. Crimped fibers may help driving the bulkiness and void volume of the nonwoven, which helps to lower the Strike-In time and MDP values.

The ADL layer, and in particular a nonwoven layer thereof, may be made or comprise of synthetic fibers. Particularly suitable synthetic fibers are made of polyolefins (e.g. polyethylene, polypropylene or mixtures or combinations thereof), polyethylene terephthalate (PET), co-PET, polylactic acid (PLA), polyhydroxy alkanoid (PHA), or combinations or mixtures thereof. The fibers may be continuous or staple fibers.

The fibers may be monocomponent fibers or multicomponent fibers, such as bicomponent fibers. If the fibers comprised by the lower ADL are bicomponent fibers, they have a core-sheath configuration, wherein the core component has a higher melting point than the sheath component.

The fibers comprised by the lower ADL are preferably staple fibers. Similar to a nonwoven web made of continuous fibers, a nonwoven web of staple fibers is preferably air-through bonded. In addition to hydroentanglement (spunlace) or air-through bonding, the nonwoven web of staple fibers may or may not have undergone some localized bonding with heat and/or pressure (e.g. point bonding/calendar bonding), introducing localized bond regions where the fibers are fused to each other.

Irrespective whether the nonwoven web is made of continuous fibers or staple fibers, the localized bonding should however not bond an excessively large surface area, thus negatively impacting the loft and void volume of the nonwoven web. Preferably, the total bond area obtained by localized bonding with heat and/or pressure (in addition to hydroentanglement or air-through bonding) should not be more than 20%, or not be more than 15%, or not be more than 10% of the total surface area of the nonwoven web.

Through-air bonding (interchangeably used with the term "air-through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The air velocity is typically between 30 and 90 meter per minute and the dwell time may be as long as 6 seconds. The melting and re-solidification of the polymer provide the bonding between different fibers.

The hot air melts the staple or continuous fiber, or, for multicomponent fibers, the lower melting polymer component of the fiber and thereby forms bonds between the staple fibers to consolidate and integrate the layer of staple fibers into a web.

The nonwoven layer comprised by or forming the lower ADL may comprise multicomponent fibers. The fibers of the nonwoven comprised by the lower acquisition and distribution layer, may comprise at least 30 weight-%, or at least 40 weight-%, or at least 50 weight-%, or at least 70 weight-%, or at least 90 weight-% or 100 weight-% of multicomponent fibers based on the total weight of the nonwoven comprised by the lower acquisition and distribution layer. The multicomponent fibers may be bicomponent fibers, such as core-sheath or side-by-side bicomponent fibers.

Alternatively, the nonwoven layer comprised by or forming the lower ADL may comprise monocomponent fibers. The fibers of the nonwoven comprised by the lower acquisition and distribution layer, may comprise at least 30 weight-%, or at least 40 weight-%, or at least 50 weight-%, or at least 70 weight-%, or at least 90 weight-% or 100 weight-% of monocomponent fibers based on the total weight of the nonwoven comprised by the lower acquisition and distribution layer. The nonwoven web comprised by or forming the lower ADL may comprise a mixture of monocomponent fiber and multicomponent fibers.

In general, the fiber dtex (linked to the fiber's diameter) is directly impacting the pore size of the material and therefore especially the capillary pressure and permeability/strike-in and strike-through of the material. At a given basis weight, the lower the dtex, the lower the permeability and higher the capillary pressure. The lower acquisition and distribution layer may comprise fibers having at least 50%, or at least 70%, or at least 80% and up to 100% by weight of fibers having a denier below 10 dtex.

The lower ADL may advantageously comprise a hydrophilic agent, especially if the lower ADL comprise or consists of synthetic fibers that are inherently hydrophobic. Any conventional hydrophilic treatments may be used to provide the hydrophilic agent. Typically, a web such as a nonwoven can be externally coated by a surfactant directly or via an oil/emulsion. Alternatively, hydrophilic melt additives can be added in the polymer melt used to make the fibers, as is known in the art. Hydrophilic melt additives are amphiphilic molecules having a hydrophilic head and a hydrophobic tail. The hydrophilic head is oriented towards the surface of the adhesive, thus providing for the hydrophilic character of the adhesive, while the hydrophobic head remains in the polymer matrix.

Hydrophilic melt additives are typically compounded in a masterbatch in the form of pellets than can be incorporated by homogenous mixing in the molten polyolefin. Commercial examples of hotmelt additives particularly compatible with a propylene-based metallocene-catalyzed polyolefin are PPM 15560 from Techmer (hydrophilic PP masterbatch) and Brij S2 (Croda). Further, in order of declining preference, Brij S10 (from Croda) Unithox 450, Unithox 720 and Unithox 750 (from Baker Hughes) can be used. PPM 15560 is preferably used in a dosage of 0.5 weight percent of the masterbatch, Brij S2 and Brij S10 in a dosage of preferably 2 weight percent of the active. Techsurf® melt additives from Techmer have been used to impart hydrophilicity to polyolefin fibers, nonwoven fabrics, and specialty plastic applications, and are useful in the present disclosure.

U.S. Pat. No. 6,146,757 discloses a hydrophilic melt additive comprising a blend of a first wetting agent and a second wetting agent. The first wetting agent is at least one water insoluble nonionic alkoxylated alkyl phenol, and the second wetting agent is at least one compound selected from the group consisting of an alkoxylated fatty alcohol and a water-soluble, nonionic, nonhydrolyzable polyoxyalkylene-modified organosilicone polymer. While not wishing to be bound by theory, it is believed that Techmer PPM 15560 is a melt additive according to this formula, in particular wherein the first wetting agent is a an ethoxylated nonylphenol having about 4 moles of ethylene oxide and the second wetting agent is a water-soluble, nonionic, non-hydrolyzable polyoxyalkylene-modified organosilicone polymer. However, this example is not limiting the present disclosure, which can be reduced in practice with other melt additives, as exemplified above.

The additives of the Brij® series from Croda are ethoxylated alcohols of the general formula:

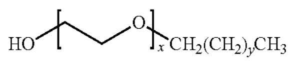

with x ranging from 2 to 100 and y ranging from 12 to 24, in particular y=16 (stearyl).

For example, Brij S2 with x=2 and y=16 has a low molecular weight of 386 g/mol, which presumably facilitates the diffusion to the surface. These ethoxylated alcohols may be a more cost-effective alternative to the above mentioned blend. The blends described in U.S. Pat. No. 6,146,757 were found to enable a stronger hydrophilic effect, while Brij S2 enables a milder hydrophilic effect. One or the other additive may be thus preferred depending on the application purpose.

The lower acquisition and distribution layer 60 and the lower substrate layer 46 may advantageously be both hydrophilic. The lower acquisition and distribution layer may be optionally less hydrophilic than the lower substrate layer.

Packages

A plurality of articles according to the present disclosure may be packaged in a package for transport and sale. At least 50% of the articles, and preferably all the articles, in the package may be according to the present disclosure. The articles may be folded and packaged as is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate number of absorbent articles per package. By packaging the absorbent articles under compression, caregivers can easily handle and store the packages, while also providing distribution and inventory savings to manufacturers owing to the size of the packages.

The absorbent articles may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Procedures. The articles before compression are sampled from the production line between the folding unit and the stack packing unit. The stack height before compression is measured by taking 10 articles before compression and packing, and measuring their stack height as indicated for the IBSH.

Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test described herein. For each of the values indicated in the previous sentence, it may be desirable to have an In-Bag Stack Height of greater than 60, or greater than 70 mm, or greater than 75 mm, or greater than 80 mm. Alternatively, packages of the absorbent articles of the present disclosure may have an In-Bag Stack Height of from 60 mm to 110 mm, from 65 mm to 110 mm, from 70 mm to 110 mm, from 75 mm to 105 mm, or from 80 mm to 100 mm, specifically reciting all 0.1 mm increments within the specified ranges and all ranges formed therein or thereby, according to the In-Back Stack Height Test described herein.

Bio-Sourced Materials

Components of the disposable absorbent article (i.e., diaper, pant, sanitary napkin, pantiliner, etc.) of the present disclosure can at least partially be comprised of bio-sourced content as described in U.S. 2007/0219521A1 Hird et al published on Sep. 20, 2007, U.S. 2011/0139658A1 Hird et al published on Jun. 16, 2011, U.S. 2011/0139657A1 Hird et al published on Jun. 16, 2011, U.S. 2011/0152812A1 Hird et al published on Jun. 23, 2011, U.S. 2011/0139662A1 Hird et al published on Jun. 16, 2011, and U.S. 2011/0139659A1 Hird et al published on Jun. 16, 2011. These components include, but are not limited to, topsheet nonwovens, backsheet films, backsheet nonwovens, barrier leg cuff nonwovens, superabsorbent material, upper and lower substrate layer, adhesives, fastener hooks, and fastener landing zone nonwovens and film based. For example, the upper and/or lower acquisition and distribution layer of the present disclosure may at least partially be comprised of bio-sourced content.

The disposable absorbent article component may comprise a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. Thereto, the disposable absorbent article component may be ground into particulates less than about 20 mesh using known grinding methods (e.g., Wiley® mill), and a representative sample of suitable mass taken from the randomly mixed particles.

EXAMPLES

Examples of Lower ADL Material

The Strike-In time, MDP and caliper at 0.85 kPa of six commercially available nonwoven materials (as described below in Table 1) were measured. The measured values are reported in Table 2.

TABLE 1

| Option | Material Description | | Basis weight [gsm] | Supplier |
|---|---|---|---|---|
| 1 | Carded Calendar bonded | 40% 2.2 dtex Trilobal PP & 60% 6.7 dtex solid round PET fibers-fully philic (both fibers surfactant treated) | 40 | Sandler |
| 2 | Carded Air-Through bonded | 60% 2.2 dtex CoPET/PET fibers & 40% 3.3 dtex hollow conjugate PET-(both fibers surfactant treated) | 40 | Yanjan |
| 3 | Carded Spunlace | CoPET/PET, PET & Viscose fibers | 40 | Yanjan |
| 4 | Carded Calendar Bonded | Trilobal PP & solid round PET fibers-partially philic (only PET fibers treated with surfactant) | 40 | Sandler |
| 5 | Carded Calendar Bonded | Trilobal PP & solid round PET fibers-partially philic (only PET fibers treated with surfactant) | 33 | Sandler |
| 6 | Carded Airthrough bonded | PE/PET bico fibers-phobic (not treated fibers) | 60 | Yanjan |

TABLE 2

| Option | Raw material properties | | |
|---|---|---|---|
| | Strike-In (1 gush) [s] | MDP [cm H2O] | Caliper at 0.85 kPa [mm] |
| 1 | 1.6 | 8.8 | 0.76 |
| 2 | 6.7 | 11.0 | 0.58 |
| 3 | 19.9 | 27.4 | 0.38 |
| 4 | 21.8 | 10.3 | 0.74 |
| 5 | 60.2 | 13.2 | 0.57 |
| 6 | >100 (stopped after 100 s) | 11.95 | 0.97 |

As can be seen, options 1-2 have properties according to the present disclosure while options 3-6 are not. The material options were then applied to make absorbent articles as described below.

Examples of Absorbent Article

Commercial Size 4 Pampers® Baby Dry market product (Western Europe, 2H 2020) were modified to include a lower acquisition and distribution layer according to examples 1-6 above (herein "sample layer"). In addition, the non-modified Size 4 Pampers Baby Dry diaper was used as comparative example.

Description of the modified absorbent article: the combination of topsheet & dual acquisition layer and absorbent core of the Pampers diapers were carefully removed using ice-spray. For each diaper, the sample layer was attached to the wearer-facing surface of the backsheet with a hotmelt adhesive applied in form of spirals with a basis weight of 5 g/m$^2$. The sample layer was cut with a width of 90 mm and was centered on the backsheet with respect to the transverse direction. The different sample layer nonwovens (mentioned in table 1 above) were used for the different modified products. The sample layer had the same length as the original absorbent core and was placed at the same position as the original absorbent core with respect to the longitudinal direction. The original absorbent core was then attached to the sample layer with a hotmelt adhesive applied in form of double sided tape with a basis weight around 25 g/m$^2$ at the center and close to the corners of the sample layer in longitudinal direction such that the absorbent core and dual acquisition layer was placed in the exact position as before removal. The absorbent core was attached to the sample layer in the longitudinal direction at the sides of the sample layer, with the front and back edges of the sample layer corresponding with the front and back edges of the absorbent core. Finally, the combination of original Topsheet and dual acquisition layer re-attached to the absorbent core with a hot melt adhesive applied in form of spirals with a basis weight of 5 g/m$^2$. The diaper samples were compacted in a flexible bag at an In Bag Stack Height, i.e. the total caliper of 10 bi-folded diapers, of 78 mm for 1 week. Then the bag was opened and the diapers out of the bag were conditioned at least 24 hours prior to any testing at 23° C.+/−2° C. and 50%+/−10% Relative Humidity (RH).

Lab Assessment of the Diapers

The diapers thus modified were tested according to the C-SABAP method and MNAS method.

C-SABAP (Curved-Speed of Acquisition with Balloon Applied Pressure) determines the time required to absorbed a predetermined amount of saline solution while the diaper is held in a slightly curved position and placed on a latex film which is inflated by pressurized air (2.07 kPa (0.30 psi)) and monitored by a digital manometer. The speed of acquisition was measured on 4 replicates for each type of diapers. Four gushes of each 75 ml of colored saline solution (0.9 w. %) were applied sequentially at a rate 15 ml/s, with 5 minutes between each gush. The speed of acquisition for each gush is recorded from the time the fluid application starts to the time when fluid is not present in the surface of the TS over the application area. The liquid is delivered in the diaper at 102 mm from the front of the absorbent core, and centered in transverse direction. Lower number of acquisition time are desired and indicate a faster absorption speed of the absorbent article.

The MNAS Test Method is used to quantify the liquid distribution in an absorbent article as a function of depth and after application of liquid insults at a position of interest in the absorbent article. The article is positioned in an apparatus that applies a constant pressure to the absorbent article, and while this pressure is applied, one or more insults of saline solution are applied to positions of interest in the absorbent article. The apparatus is additionally positioned with a low-field NMR instrument such that the instrument is capable of measuring liquid depth profiles of the absorbent article while under pressure. From these liquid depth profiles, depth zones of interest are defined, quantified, and reported. The general NMR test method and apparatus are also described in U.S. Pat. Nos. 10,371,652 and 10,365,237.

In addition to diapers modified with a layer according to options 1-6 above, unmodified Pampers Baby Dry diapers was also tested as option 7. The results obtained are shown in Table 3 below.

TABLE 3

| | C-SABAP method | | | | MNAS | |
|---|---|---|---|---|---|---|
| Option | 1 Gush [s] | 2 Gush [s] | 3 Gush [s] | 4 Gush [s] | mL fluid at bottom 50-200 mm | mL fluid at bottom 250-400 mm |
| 1 | 33 | 33 | 45 | 95 | 3.2 | 3.7 |
| 2 | 33 | 38 | 52 | 103 | 3.5 | 4.0 |
| 3 | 39 | 41 | 57 | 108 | 5.7 | 10.8 |
| 4 | 37 | 40 | 55 | 106 | 3.1 | 5.0 |
| 5 | 37 | 40 | 61 | 122 | 3.2 | 4.0 |
| 6 | 40 | 44 | 66 | 129 | 3.4 | 2.0 |
| 7 | 40 | 38 | 54 | 119 | 6.3 | 16.6 |

Examples 1-2, which are according to the present disclosure, were the only samples to combine superior C-SABAP value across the 4 gushes and MNAS values relative to the other examples and the reference diaper of option 7.

While not wishing to be bound by theory, the inventors believe that lower values for the Strike-In time characterize material with faster speed of acquisition when used as the bottom temporary storage layer. The Strike-In time reflects the contribution of reduced surface energy on the fibers/filaments, increased permeability of the layer and increased void space in the substrate. Strike-In Values below 10 seconds for materials with a caliper of 0.3 mm or higher provide improved overall acquisition speed for the absorbent article. Lower MDP values indicate material that are easier to drain, having tendency to store less liquid directly behind the backsheet.

The data generated confirm that the parameters claimed, when balanced properly, can break the tension between dryness perception negatives from the outer backsheet layer (measured as mL of fluid within 250 μm from the outer cover surface using MNAS) and acquisition benefits (measured as mL/s of fluid acquired by the core using a cGAM protocol), and enable development and selection of unique materials for such application.

Test Methods

Strike-In Test Method

The Strike-In Test Method is used to determine absorption behavior of porous materials. This test method measures the Strike-In time, i.e. the time taken for a known volume of liquid (simulated urine) applied to the surface of a test portion of nonwoven (or other porous material tested), which is in contact with a base plate, to acquire into the material. This test method is designed to compare Strike-In time of different nonwovens.

Reference: the Strike-In Test Method is a modification of EDANA NWSP 070.3 R1 (19) "Strike-Through" method, and uses the same measuring equipment as described in EDANA WSP 070.3 R1 (19).

Terms and Definitions: the following referenced terms are of utility for the application of this document:

Sample: for testing purposes a product or a portion of a product taken from a production lot. The sample shall be identifiable and traceable back to the origin.

Simulated urine: A testing liquid consisting of a 9 g/l solution of sodium chloride in distilled water with a surface tension of 72 (±1) mN/m. This surface tension should be checked before each series of tests, as surface tension can alter during storage.

Specimen: A specific portion of the identified sample upon which a test is performed. Many specimens may be tested from the same sample, using different locations.

Principle: A specified quantity (3 ml) of simulated urine is discharged at a prescribed rate under specified conditions onto a test specimen. The time taken for the entire liquid dose to penetrate the specimen is measured electronically.

Apparatus

Burette: this has a 50 ml capacity and is attached to a supporting stand.

Funnel: fitted with a magnetic valve, giving a rate of discharge of 25 ml in 3.5 (±0.25) s.

Ring stand: to support the funnel.

Strike-through plate (see FIGS. 1 and 2 EDANA NWSP 070.3 R1(19)): constructed of 25 mm thick transparent acrylic sheet, of total mass (500±5 g), fitted with corrosion-resistant electrodes consisting of 1.6 mm diameter platinum or stainless steel wire set in grooves of cross-section 4.0 mm×7.0 mm cut in the base of the plate and fixed with quick-setting epoxy resin. The electrodes shall be positioned as shown in FIGS. 1 and 2.

Baseplate: made of transparent acrylic sheet, approximately 125 mm×125 mm square and 5 mm thick.

Electronic timer: Which can be read to the nearest 0.01 s.

Note:

This complete machine can be purchased from: W. Fritz Mezger, Inc., 155 Hall St. Spartanburg, SC 29302

Sample conditioning and specimen preparation: the Strike-In Test Method is conducted on samples that have been conditioned in a room at a temperature of 23° C.±2.0° C. and a relative humidity of 50%±5%, all tests are conducted under the same environmental conditions and in such conditioned room. Any damaged product or samples that have defects such as wrinkles, tears, holes, and similar are not tested. Samples conditioned as described herein are considered dry samples for purposes of the present disclosure.

Specimens are measured for any given material being tested, and the results from those three replicates are averaged to give the final reported value. Each of the replicate specimens has a cut length of 100 mm×90 mm Procedure:

Set up the ring stand, by positioning the burette with the tip inside the funnel.

Cut the required number of specimens 100 mm×90 mm

Place one test specimen on the base plate. Place the specimen on the base plate in such a way that the side of the specimen, which is intended to be facing to the absorbent core/direction to user's skin, is uppermost. Ensure that the electrodes in the strikethrough plate are clean. Place the strike-through plate on top of the specimen with the center of the plate over the center of the test specimen. Center the burette and the funnel over the plate.

Adjust the height of the funnel so that the funnel is 5 (±0.5) mm above the top of the cavity in the plate (i.e. 30 mm above the test specimen).

Ensure the electrodes are connected to the timer

Activate the timer and set the clock to zero.

Fill the burette with simulated urine, keep the discharge valve of the funnel closed and run 3.0 ml of liquid from the burette into the funnel.

Open the magnetic discharge valve of the funnel to discharge 3.0 ml of liquid. The initial flow of liquid will complete the electrical circuit and start the timer. It will stop when the liquid has penetrated into the nonwoven and fallen below the level of the electrodes in the strike-through plate.

Record the time indicated on the electronic timer.

Calculation: Calculate average time for 5 repeats.

Capillary Sorption Test Method

The Capillary Sorption Test Method is used to determine absorption and desorption behavior of porous materials, and specifically the Median Desorption Pressure (MDP). This method makes use of stepped, controlled differential pressure and measurement of associated fluid movement into and out of a porous specimen. The Median Desorption Pressure is the differential pressure at which the material has 50% of its Maximum Normalized Capillary Fluid Absorbed or Desorbed (NCFAD) in the desorption phase of the measurement and is expressed in cmH2O (1 $cmH_2O$=98.063 Pa).

Method Principle

For uniform cylindrical pores, the radius of a pore is related to the differential pressure required to fill or empty the pore by the equation $$\text{Differential pressure}=(2\gamma \cos \Theta)/r;$$

where γ=liquid surface tension, Θ=contact angle, and r=pore radius.

Pores contained in natural and manufactured porous materials are often thought of in terms such as voids, holes or conduits, and these pores are generally not perfectly cylindrical nor all uniform. One can nonetheless use the above equation to relate differential pressure to an effective pore radius, and by monitoring liquid movement into or out of the material as a function of differential pressure characterize the effective pore radius distribution in a porous material. (Because nonuniform pores are approximated as uniform by the use of an effective pore radius, this general methodology may not produce results precisely in agreement with measurements of void dimensions obtained by other methods such as microscopy.)

The Capillary Sorption Test Method uses the above principle and is reduced to practice using the apparatus and approach described in "Liquid Porosimetry: New Methodology and Applications" by B. Miller and I. Tyomkin published in The Journal of Colloid and Interface Science (1994), volume 162, pages 163-170, incorporated herein by reference. This method relies on measuring the increment of liquid volume that enters or leaves a porous material as the differential air pressure is changed between ambient ("lab") air pressure and a slightly elevated air pressure (positive differential pressure) surrounding the specimen in a sample test chamber. The specimen is introduced to the sample chamber dry, and the sample chamber is controlled at a positive differential pressure (relative to the lab) sufficient to prevent fluid uptake into the specimen after the fluid bridge is opened. After opening the fluid bridge, the differential air pressure is decreased in steps to 0, and in this process subpopulations of pores acquire liquid according to their effective pore radius. After reaching a minimal differential pressure at which the mass of fluid within the specimen is at a maximum, differential pressure is increased stepwise again toward the starting pressure, and the liquid is drained from the specimen. It is during the desorption sequence (from minimal differential pressure, or largest corresponding effective pore radius, to the maximum differential pressure, or smallest corresponding effective pore radius), that the fluid desorption by the sample (g/g) at each differential pressure is determined in this method. After correcting for any fluid movement for each particular pressure step measured on the chamber while empty, the fluid desorption by the sample (g/g) for each pressure step is determined via dividing the equilibrium quantity of absorbed liquid (g) associated with this particular step by the dry weight of the sample (g).

Sample Conditioning and Specimen Preparation

The Capillary Sorption Test Method is conducted on samples that have been conditioned in a room at a temperature of 23° C.±2.0° C. and a relative humidity of 50%±5%, all tests are conducted under the same environmental conditions and in such conditioned room. Any damaged product or samples that have defects such as wrinkles, tears, holes, and similar are not tested. Samples conditioned as described herein are considered dry samples for purposes of the present disclosure. Three specimens are measured for any given material being tested, and the results from those three replicates are averaged to give the final reported value. Each of the three replicate specimens has a diameter of 50 mm.

Apparatus

Apparatus suitable for this method is described in: "Liquid Porosimetry: New Methodology and Applications" by B. Miller and I. Tyomkin published in The Journal of Colloid and Interface Science (1994), volume 162, pages 163-170. Further, any pressure control scheme capable of controlling the sample chamber pressure between 0 mmH2O and 1200 mmH2O differential pressure may be used in place of the pressure-control subsystem described in this reference. One example of suitable overall instrumentation and software is the TRI/Autoporosimeter (Textile Research Institute (TRI)/Princeton Inc. of Princeton, N.J., U.S.A.). The TRI/Autoporosimeter is an automated computer-controlled instrument for measuring pore volume distributions in porous materials (e.g., the volumes of different size pores within the range from 1 to 1000 μm effective pore radii). Computer programs such as Automated Instrument Software Releases 2000.1 or 2003.1/2005.1 or 2006.2; or Data Treatment Software Release 2000.1 (available from TRI Princeton Inc.), and spreadsheet programs may be used to capture and analyze the measured data.

Method Procedure

The wetting liquid used is a degassed 0.9% NaCl solution. Liquid density is 1.01 $g/cm^3$, surface tension γ to be 72.3 (±1) mN/m, and the contact angle cos Θ=0.37. A 90-mm diameter mixed-cellulose-ester filter membrane with a characteristic pore size of 1.2 μm (such Millipore Corporation of Bedford, MA, Catalogue #RAWP09025) is affixed to the porous frit (Monel plates with diameter of 90 mm, 6.4 mm thickness from Mott Corp., Farmington, CT, or equivalent) of the sample chamber.

The test fluid as well as the frit/membrane/tubing system are degassed such that the system is free from air bubbles.

A metal weight weighing 414 g is placed on top of the sample to exert a constant confining pressure of 2.068 kPa during measurement.

The sequence of differential pressures that are run in the test, in mmH2O, is as follows: 800, 700, 650, 600, 550, 500, 450, 400, 380, 360, 340, 320, 300, 280, 265, 250, 235, 220, 205, 190, 175, 160, 145, 130, 115, 100, 90, 80, 70, 60, 55, 50, 45, 40, 35, 30, 25, 20, 15, 10, 5, 0, 5, 10, 15, 20, 25, 30, 35, 40, 45, 50, 55, 60, 70, 80, 90, 100, 115, 130, 145, 160, 175, 190, 205, 220, 235, 250, 265, 280, 300, 320, 340, 360, 380, 400, 450, 500, 550, 600, 650, 700, 800.

The criterion for moving from one pressure step to the next is that fluid uptake/drainage from the specimen is measured to be less than 10 mg/min for 15 s.

A separate "blank" measurement is performed by following this method procedure on an empty sample chamber with no specimen or weight present on the membrane/frit assembly. Any fluid movement observed is recorded (g) at each of the pressure steps. Fluid absorption/retention data for a specimen are corrected for any fluid movement associated with the empty sample chamber by subtracting fluid absorption/retention values of this "blank" measurement from corresponding values in the measurement of the specimen.

Determination of Median Desorption Pressure (MDP)

As described above, for each of the three specimens, the capillary fluid absorbed and then desorbed (g) by each specimen during its absorption and desorption cycle is corrected for any effect of the empty chamber and then divided by the dry mass of the specimen to arrive at capillary fluid absorbed or desorbed normalized by dry sample mass in units of g/g. This is referred to as the normalized capillary fluid absorbed or desorbed (NCFAD). The NCFAD is in units of g/g and is calculated for each differential pressure step. The NCFAD is a cumulative parameter. For example, the value of NFCAD at 300 mmH2O on the uptake portion of the pressure sequence is the total fluid in g/g that has been absorbed between 800 mmH2O and 300 mmH2O and likewise for all other points. We note that NCFAD generally increases on the first, absorption portion of the measurement cycle, with each incremental step increasing its value. Similarly, the NCFAD generally decreases on the second, desorption portion of the measurement cycle with each desorption step decreasing the cumulative NCFAD parameter as fluid is desorbed from the specimen. The Maximum NCFAD for fluid uptake is the value of NCFAD at 0 mmH2O.

The Median Desorption Pressure (MDP) is the differential pressure at which the material has 50% of its Maximum NCFAD in the fluid desorption portion of the measurement (second half of pressure sequence specified) and is expressed in mmH2O. If the value of NCFAD is not exactly 50% for any pressure step in the sequence of pressures, a linear interpolation is made between the two neighboring pressures for which NCFAD spans 50% (one above and below) to arrive at MDP for a particular specimen.

The arithmetic mean of three values for MDP for the three specimens is calculated and converted from pressure units of mmH2O to units of cmH2O and is reported as the overall parameter MDP in cmH2O.

Caliper Measurement Method

The caliper of the lower ADL is determined using the Caliper Test Method. In the Caliper Test Method, two flat, parallel surfaces are used to apply unidirectional pressure to both sides of a substrate specimen, and the resulting separation between the parallel surfaces is measured. All measurements are performed in a laboratory maintained at 23±2° C. and 50±2% relative humidity and test specimens are conditioned in this environment for at least 2 hours prior to testing.

One suitable example of apparatus for use in the Caliper Method is a Mitutoyo Digimatic Series 543 ID-C digital indicator (Mitutoyo America Corp., Aurora, Illinois, USA), or equivalent, fitted with a circular flat "foot" having a diameter of 4.0 cm at the end of the moving shaft of the indicator gauge. The indicator is mounted on a horizontal granite base such that the shaft of the indicator gauge is oriented vertically, and the plane of the circular foot is parallel to the granite base. The circular foot is sized and weighted such that the gravitational force associated with the mass of the foot and the indicator shaft together divided by the area of the circular foot constitutes 0.85 kPa of downward pressure from the circular foot on the granite base. Specimens at least as large as the circular foot are analyzed between the circular foot and granite base.

The caliper is measured 20 s after the round foot has been contacted with the specimen. For a given material, 10 specimens from this material are measured and the average value reported as the caliper of the material.

Misc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

a liquid-permeable topsheet;

a liquid-impermeable backsheet;

an absorbent material between the topsheet and the backsheet, the absorbent material comprising a superabsorbent polymer, wherein the absorbent material is disposed between an upper substrate layer and a lower substrate layer, wherein the absorbent material comprises a pair of partially longitudinally extending channels which are free of absorbent material; and a lower acquisition and distribution layer disposed between the absorbent material and the backsheet;

wherein the lower acquisition and distribution layer has a Strike-In between 1.6 seconds and 8 seconds, as measured by the Strike-In test, and a Median Desorption Pressure (MDP) of less than 20 cmH2O, as measured by the Capillary Sorption Test Method;

wherein at least 30% by weight of the lower acquisition and distribution layer comprises crimped fibers, and wherein the crimped fibers have two-dimensional crimp, three dimensional crimp, or a combination of two- and three-dimensional crimp; and wherein either:

the lower acquisition and distribution layer is disposed between the lower substrate layer and the backsheet; or the lower acquisition and distribution layer and the lower substrate layer are the same layer; or the lower acquisition and distribution layer is disposed between the absorbent material and the lower acquisition substrate layer.

2. The absorbent article according to claim 1, wherein the lower acquisition and distribution layer has a Median Desorption Pressure of less than 15 cmH2O.

3. The absorbent article according to claim 2, wherein the lower acquisition and distribution layer has a Median Desorption Pressure of from 8.8 cmH2O to 15 cmH2O.

4. The absorbent article according to claim 1, wherein the lower acquisition and distribution layer has a caliper of at least 0.3 mm, and up to 4 mm, as measured at 0.85 kPa pressure according to the Caliper Measurement Method.

5. The absorbent article according to claim 1, wherein the lower acquisition and distribution layer comprises a nonwoven layer.

6. The absorbent article according to claim 1, wherein the lower acquisition and distribution layer comprises a carded nonwoven layer.

7. The absorbent article according to claim 1, wherein the lower acquisition and distribution layer comprises fibers, and wherein at least 50% by weight of the fibers have a denier below 10 dtex.

8. The absorbent article according to claim 1, wherein the lower acquisition and distribution layer comprises a hydrophilic agent.

9. The absorbent article according to claim 8, wherein the hydrophilic agent is a surfactant coating, or a hydrophilic melt additive, or both.

10. The absorbent article according to claim 1, wherein the lower acquisition and distribution layer has a basis weight of from 20 gsm to 100 gsm.

11. The absorbent article according to claim 10, wherein the lower acquisition and distribution layer has a basis weight of from 30 gsm to 50 gsm.

12. The absorbent article according to claim 1, wherein the absorbent material does not comprise cellulose fibers mixed with superabsorbent polymer particles.

13. The absorbent article according to claim 1, wherein at least 50% of the length of the channel is vertically superposed with the lower acquisition and distribution layer.

14. The absorbent article according to claim 1, wherein the lower acquisition and distribution layer consists of a single nonwoven layer.

15. The absorbent article according to claim 1, wherein the upper substrate layer and the lower substrate layer are at least longitudinally bonded to each other.

16. The absorbent article according to claim 1, wherein the lower acquisition and distribution layer and the lower substrate layer are both hydrophilic, and wherein the lower acquisition and distribution layer is less hydrophilic than the lower substrate layer.

* * * * *